(12) United States Patent
Tofail et al.

(10) Patent No.: US 7,799,268 B2
(45) Date of Patent: Sep. 21, 2010

(54) IMPLANTS

(75) Inventors: Syed Ansar Md Tofail, Limerick (IE); Donncha Haverty, County Tipperary (IE)

(73) Assignee: University of Limerick, Limerick (IE)

( * ) Notice: Subject to any disclaimer, the term of this patent is extended or adjusted under 35 U.S.C. 154(b) by 552 days.

(21) Appl. No.: 11/487,483

(22) Filed: Jul. 17, 2006

(65) Prior Publication Data

US 2007/0040478 A1 Feb. 22, 2007

Related U.S. Application Data

(60) Provisional application No. 60/700,322, filed on Jul. 19, 2005.

(51) Int. Cl.
*B28B 1/00* (2006.01)
(52) U.S. Cl. .................................................... 264/675
(58) Field of Classification Search ................ 264/675
See application file for complete search history.

(56) References Cited

U.S. PATENT DOCUMENTS

| | | | | |
|---|---|---|---|---|
| 4,900,832 | A * | 2/1990 | Parris et al. | 546/186 |
| 5,990,381 | A * | 11/1999 | Nishihara | 424/422 |
| 6,777,214 | B1 | 8/2004 | Yamashita | 435/173.1 |
| 2003/0059742 | A1* | 3/2003 | Webster et al. | 433/201.1 |
| 2005/0013973 | A1* | 1/2005 | Richter et al. | 428/158 |

FOREIGN PATENT DOCUMENTS

WO WO96/39202 12/1996

OTHER PUBLICATIONS

Kobayashi, Takayuki et al. "Vectoral Effects on Tissue Reaction of Electrically Poled Hydroxyapatite Ceramics" Bioceramics, vol. 12 (Oct. 1999) pp. 291-294.*
Marino et al, Calc. Tiss. Res. 8, 1971, pp. 177-180, Origin of the Piezoelectric Effect in Bone.
Kay et al, Nature, vol. 204, Dec. 12, 1964, pp. 1050-1052, Crystal Structure of Hydroxyapatite.
Elliott et al, Science vol. 180, Jun. 8, 1973, pp. 1055-1057, Monoclinic Hydroxyapatite.
Messing et al, Critical Reviews . . . 29, 2004, pp. 45-96, Templated Grain Growth of Textured Piezoelectric Ceramics.
Gjelsvik, J. Biomechanics, vol. 6, 1973, pp. 69-77, Bone Re-modeling and Piezoelectricity-I.
Jianqing et al, Biomaterials 18, 1997, pp. 1531-1534, Promotion of osteogenesis by a piezoelectric biological ceramic.
Becker, Mechanics of Growth Control, Chpt. 11, 1981, pp. 192-210, Piezoelectricity of Bone and Osteogenesis by . . . .
Haverty et al, Physical Reviews B 71, 2005, pp. 094103-1-094103-9, Structure and stability of hydroxyapatite: Density . . . .
Tofail et al, Ferroelectrics 319, 2005, pp. 117-123, Structural Order and Dielectric Behaviour of Hyroxyapatite.
Silva et al, Materials Sci. & Eng. B86, 2001, pp. 210-218, Collagen-hydroxyapatite films: piezoelectric properties.

* cited by examiner

*Primary Examiner*—Jason L Lazorcik
*Assistant Examiner*—Russell J Kemmerle, III
(74) *Attorney, Agent, or Firm*—Jacobson Holman PLLC

(57) ABSTRACT

A piezoelectric device is produced by providing a material having a hydroxyapatite (HA) component. The HA component is textured by, for example uniaxial pressing, to impart one of the limiting symmetries ∞, ∞ mm, or ∞2. The textured material may then be poled to enhance the piezoelectric properties.

12 Claims, 7 Drawing Sheets

Crystallite ⟶ Textured composite + Polarising field ⟶ Poled composite

IMPLANTS

This is a complete application claiming benefit of provisional 60/700,322 filed Jul. 19, 2005.

INTRODUCTION

1. Field of the Invention

The invention relates to piezoelectric devices for applications such as bone and dental implants as well as ultrasonic, opto-acoustic and other electrical and electromechanical devices that may be used for sensing purposes for example.

2. Prior Art Discussion

The hierarchical structure of bone is composed of nanocrystalline-carbonated apatite, collagen fibres (a triple helix polypeptide based protein) and mucopolysaccharides. It has been known for some time that bone possesses piezoelectric properties. The proposition that bone piezoelectricity originates from collagen fibre found experimental evidence when Marino and Becker [1] measured piezoelectricity in dematerialized bone, but could not find piezoelectricity in de-collagenated bone. Despite extensive experimental and theoretical works in the past the origin of bone piezoelectricity is not well understood.

The crystal structure of hydroxyapatite, $Ca_5(PO_4)_3OH$, (henceforth HA), closely resembles that of bone apatite. Single crystal X-ray diffraction studies have suggested two phases for HA, a hexagonal $P6_3/m$ [2] where the hydroxyl ions are disordered, and a monoclinic $P2_1/b$ [3], where the hydroxyl ions are oriented anti-parallel to each other. In both cases, these structures possess a centre of symmetry and hence preclude any piezoelectricity.

Mention of the piezoelectric properties of HA crystals are made in reference [4].

Unfortunately HA is extremely difficult to obtain as single crystals of sufficient size to be of any practical use in this regard. In all technologically important applications as in for example the medical device sector, HA is used as a composite material comprising crystallites in the nano to micron scale ranges, whether as deposited coatings on substrates or as dense or porous bodies such as sintered or glass ceramics containing HA.

With regard to piezoelectric and pyroelectric materials in general, while the absence of a centre of symmetry in the individual crystallites or crystals is a necessary condition, it is not however sufficient to render a device made of such crystallites/crystals piezoelectric or pyroelectric. The role of texture and domain orientation in conventional piezoelectric ceramics such as PZT, $BaTiO_3$ and $KNbO_3$ has been well established [5]. However, the crystallites that comprise these ceramics generally have a large number of spontaneous polarisation directions that can easily be manipulated with for example the application of an electric field, as these materials are generally also ferroelectric.

The significance of piezoelectricity in the bone remodelling process is well established [6] and a number of conventional piezoelectric materials including Barium Titanate [7] and a number of piezoelectric polymers [8] when used as implant materials have been shown to promote protein adsorption and osteogenesis in vitro and in vivo. The exploration of these materials for implant applications is a logical consequence of the known piezoelectric properties of bone itself given that a biomimetic material is desired.

It is also known [9] in the art that surface charges on hydroxyapatite ceramics affects and differentiates the adsorption of proteins at these surfaces. In such cases the surface charge was generated by poling a HA ceramic. Differences in behaviour were observed depending on whether the surface was positively or negatively charged.

The present invention aims to provide improved piezoelectric devices comprising HA.

REFERENCES

[1] Marino, A. A. and Becker R. O., Calc. Tiss. Res., 8: p. 177-180, (1971).

[2] Kay, M. Young, R., Posner, A., Nature, 204, 1050-52 (1964).

[3] Elliot, J. C., Mackie P. E., Young R. A., Science, 180, 1055, (1973).

[4] PCT/US96/08652

[5] Messing, G. L., et al. Templated Grain Growth of Textured Piezoelectric Ceramics, Critical Reviews in Solid State and Materials Sciences, 29, 45-96 (2004).

[6] Gjelsvik, A. Bone remodelling and piezoelectricity I. J. Biomechanics, 6, 69-77, (1973)

[7] Jianqing, F., Y. Huipin, and Z. Xingdong, Promotion of osteogenesis by a piezoelectric biological ceramic, Biomaterials, 18, 1531-1534 (1997).

[8] Fukada E. Piezoelectricity of bone and osteogenesis by piezoelectric films in Mechanisms of growth control, R. O. Becker (ed.), 1981, Charles C Thomas: Illinois.

[9] U.S. Pat. No. 6,777,214

SUMMARY OF THE INVENTION

In one aspect, the invention provides a piezoelectric device comprising HA wherein the HA component has one of the overall limiting symmetry $\infty$ mm, $\infty 2$, or $\infty$.

In one embodiment, the HA component is anisotropic.

In one embodiment, the anisotropy is over 5%

In one embodiment, the device is a film or coating.

In one embodiment, the device is a film or coating on an implant.

In one embodiment, the implant is made of titanium, titanium alloys, stainless steel, cobalt chromium alloys, hydroxyapatite, calcium phosphate, calcium carbonate, bioglass, glass-ceramic, or ceramic In one embodiment, the device is a ceramic, either dense or porous.

In one embodiment, the ceramic contains Barium Titanate, Lead Zirconium Titanate, Potassium Niobate, Sodium Niobate, Potassium dihydrogen phosphate, Zinc oxide, Silica, Alumina, zeolite, Calcium phosphate, Calcium carbonate, Titanium dioxide, Zirconium oxide, Calcium titanate or Sodium titanate.

In one embodiment, the implant comprises a polymeric material.

In one embodiment, the device is a composite comprising HA.

In one embodiment, the device is a lamellar, dispersoid or fibre composite.

In one embodiment, the composite is porous.

In one embodiment, the composite comprises Barium Titanate, Lead Zirconium Titanate, Potassium Niobate, Sodium Niobate, Potassium dihydrogen phosphate, Zinc oxide, Silica, Alumina, zeolite, Calcium phosphate, Calcium carbonate, Titanium dioxide, Zirconium oxide, Calcium titanate, Sodium titanate, Poly-vinylidene flouride, Polycarbonate, Teflon, Poly-acrylates, Poly-glutamates, Poly-Lactic acids, Collagen, Chitosan or Cellulose.

In one embodiment, the device is pyroelectric.

In one embodiment, the device is a therapeutic device.

In one embodiment, the device is a bone, dental or a soft-tissue implant.

In one embodiment, the device is an ultrasonic or microwave transducer.

In one embodiment, the device is an opto-acoustic device.

In another aspect, the invention provides a method of producing a piezoelectric device, the method comprising the steps of
a. providing a material comprising an HA component, and
b. texturing the material by orienting the HA so as to impart one of the limiting symmetries ∞ mm, ∞, or ∞2 to the HA component.

In one embodiment, the material is textured by uniaxial pressing so as to impart one of the limiting symmetries ∞ mm, ∞, or ∞2 to the HA component.

In one embodiment, the uniaxial pressing comprises application of a uniaxial pressure between 30 MPa and 250 MPa, and preferably between 50 MPa and 150 MPa.

In one embodiment, the uniaxially pressed material is fired between 800° C. and 1700° C., preferably between 1000° C. and 1300° C.

In one embodiment, the uniaxially pressed material is fired in a steam environment.

In one embodiment, an electric field is applied during firing.

In one embodiment, an electric field is applied in an environment of ionised gas during firing In one embodiment, the electric field is lower than the dielectric breakdown voltage of the material between 0.1 kVcm$^{-1}$ and 90 kVcm$^{-1}$.

In another embodiment, the textured material is poled.

In one embodiment, the poling step comprises heating the material to a poling temperature, holding the material at the poling temperature for a poling period, and cooling the device back to a starting temperature.

In one embodiment, the poling temperature is between 40° C. and 650° C., and preferably between 150° C. and 450° C.

In one embodiment, the poling period is between 0.25 hr and 6 hr and preferably between 0.5 hr and 2.0 hr.

In one embodiment, an electric field is applied to the device for the duration of the poling period and during cooling.

In one embodiment, the electric field is lower than the dielectric breakdown voltage of the device between 0.1 kVcm$^{-1}$ and 90 kVcm$^{-1}$.

In one embodiment, the material is faceted after texturing at 0°, 45°, or 90° to a texturing direction.

DETAILED DESCRIPTION OF THE INVENTION

The invention will be more clearly understood from the following description of some embodiments thereof, given by way of example only with reference to the accompanying drawings in which:—

Figure 5:
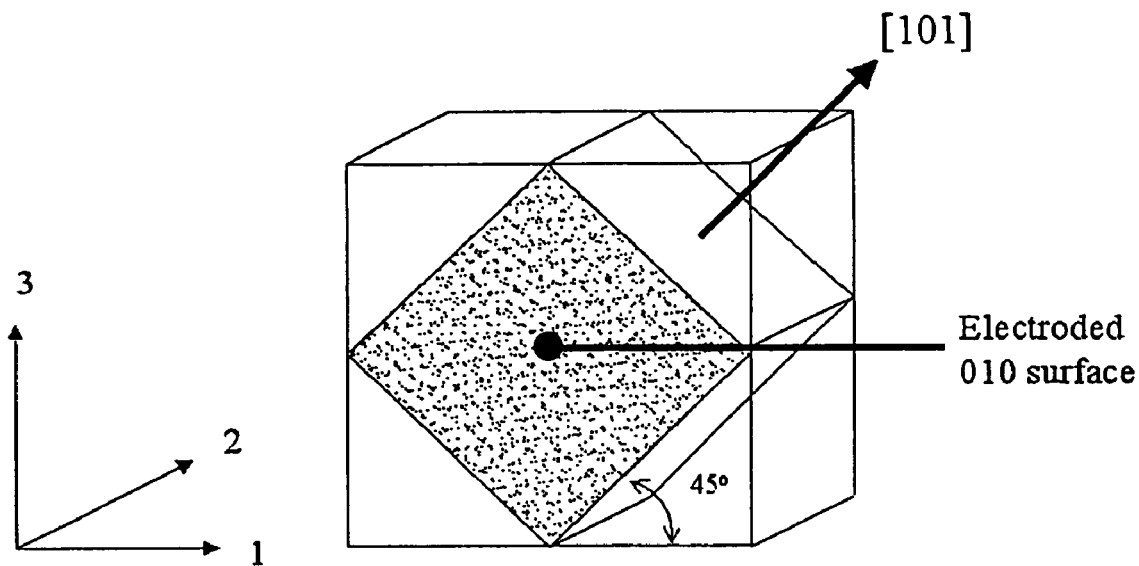
Figure 6:
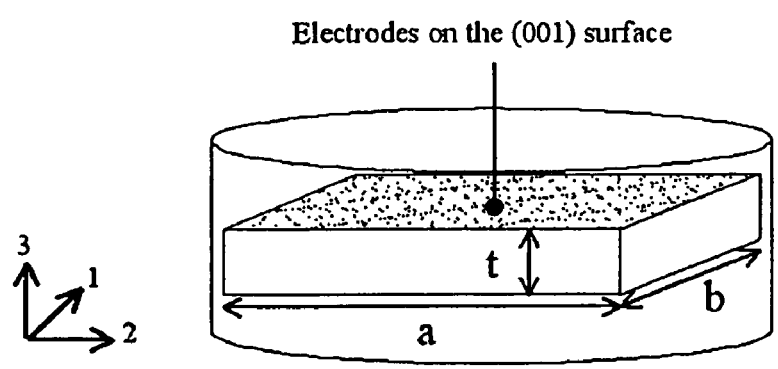
Figure 7:
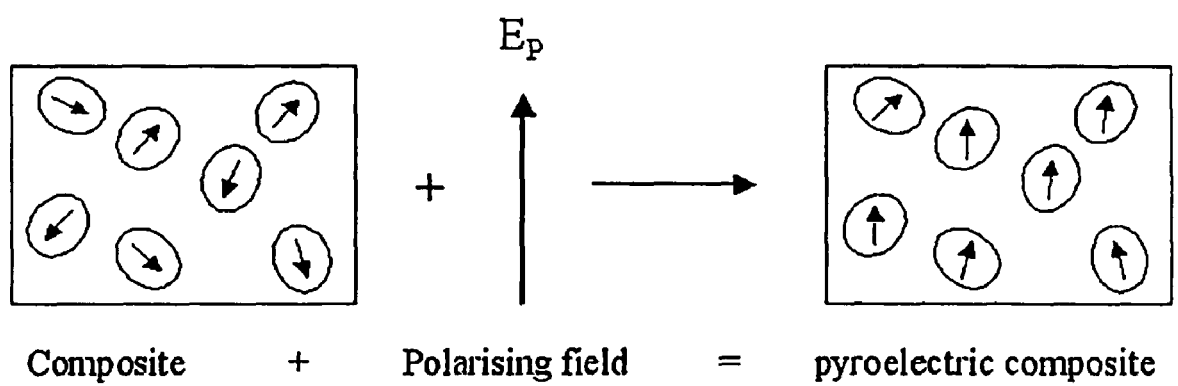

FIGS. 4(a) to 4(c) are a set of diagrams showing the transformation of single crystal tensors in the case where P2$_1$ single crystals are oriented in a plane perpendicular to the pressing direction of a HA device (a), deviation φ from axes X$_1$ and X$_2$ so that the new axes become X$_1$' and X$_2$' (c), and the transformation matrix to find the new axes (c);

FIG. 5 is a diagram that shows the orientation dependence of piezoelectric constants in a polycrystalline HA ceramic belonging to ∞2 limiting group symmetry;

FIG. 6 is a diagram showing the [001] direction in a HA disk. That has been uniaxially pressed along the '3' direction, and a rectangular plate of length 'a', width 'b' and thickness 't' can be cut from this disk and can be electroded on the 'ab' plane, which is the (001) surface;

FIG. 7 is a diagram explaining the pyroelectric effect; and

Figure 8:
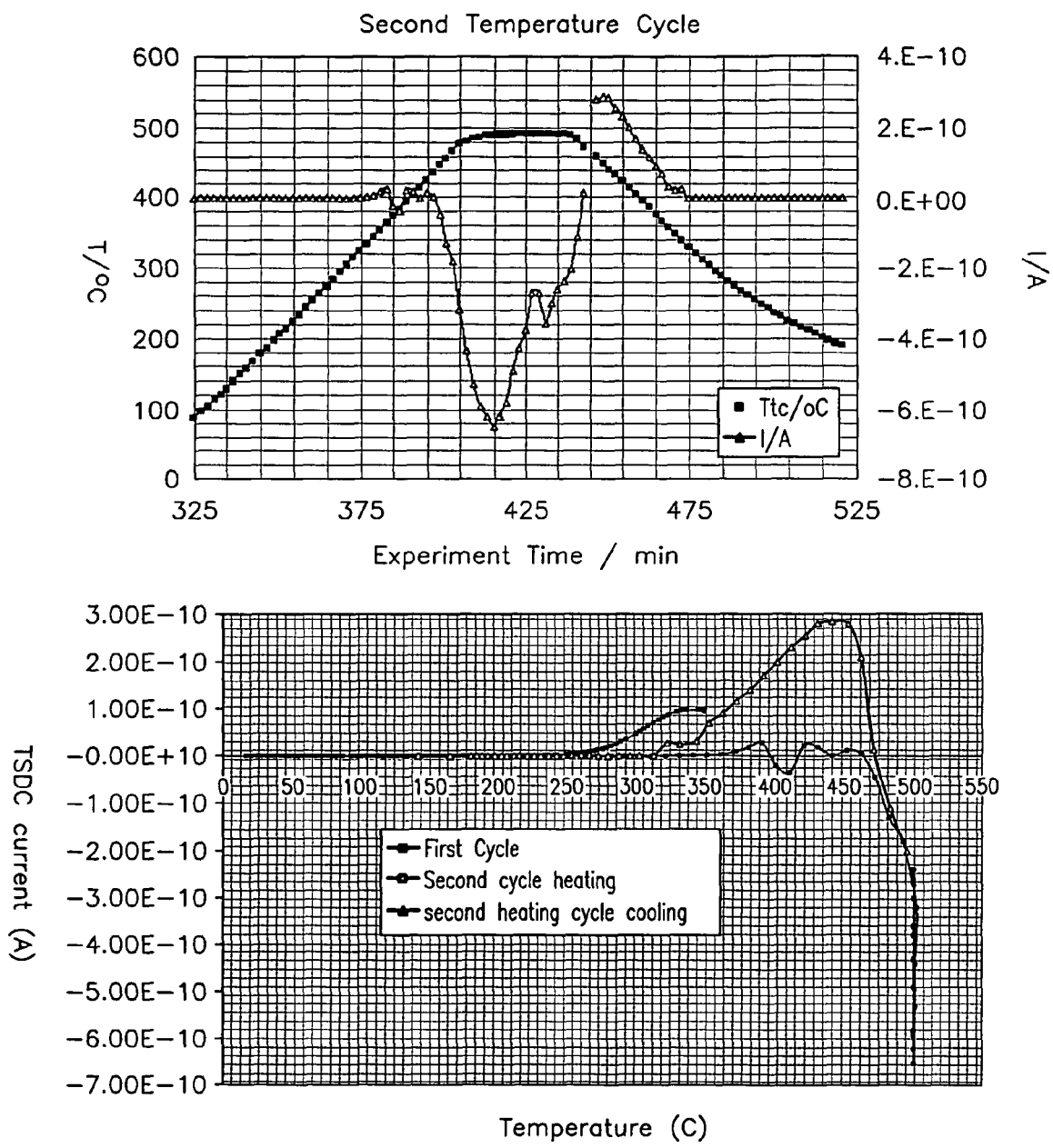

FIG. 8 shows a time-temperature-current plot showing second TSDC cycle applied to a HA disk poled along the [001] direction (top), and measured current profile comparison with the first cycle (bottom).

DESCRIPTION OF THE EMBODIMENTS

Our invention involves our understanding that hydroxyapatite ("HA"), whether as a ceramic body, ingredient in a composite, or deposited as a coating on a substrate, as well as being biocompatible and bioactive, could also with suitable treatment be piezoelectric and possibly also pyroelectric. This provides a superior biomimetic implant for example.

HA is initially textured to enhance its piezoelectric properties and is then further poled to further enhance these properties.

A single crystal of HA has a random distribution of domains of spontaneous polarisation with an overall polarisation equalling to zero. In technological applications such as deposited coatings, dense bodies and composite devices comprising non-centrosymmetric HA crystallites, the random orientation of the single crystallites precludes harnessing the piezoelectric or pyroelectric potential of the non-centrosymmetric HA in such applications.

Texturing the HA engineers the material so that the randomness of the composite decreases and there exists some degree of orientation of the crystallites comprising the device The direction of orientation is called the "texturing direction". The method of orienting crystallites or grains along a certain direction or in a certain plane in a polycrystalline device is referred to as "texturing". When this orientation is achieved along a certain direction, the composite is said to have a 'fibre texture'. When the crystallites are oriented in a plane, the composite is said to possess a 'sheet texture'. The overall symmetry of these textured devices is different to their single crystal symmetries. Instead of standard 'point group' symmetries that describe single crystals, the symmetries of polycrystalline devices are described using the Curie 'limiting group' symmetries. As is the case with point group symmetries, only a subset of these limiting group symmetries is consistent with the phenomena of piezoelectricity and or pyroelectricity.

In the case of HA single crystallites only two spontaneous polarisation directions exist. As a result, a significant proportion of the crystallites comprising a device must be aligned or oriented along a limited number of specific directions in order for piezoelectric and pyroelectric properties to be manifest in the device. In addition the device is engineered to impart the relevant Curie limiting group symmetry to the device.

As stated above, the piezoelectric and pyroelectric properties can further be improved by a subsequent poling treatment. The extent to which these treatments are used depends on the specific application. The piezoelectric and possibly also pyroelectric properties of these devices can be tailored according to the needs of a specific application.

Since piezoelectricity enhances bone growth and controls bone remodelling, an implant comprising HA as a single component or as a constituent, or coated with a HA film and treated in a manner that induces and tailors its piezoelectric properties is advantageous when compared to the non-piezoelectric HA implants.

Figure 1:
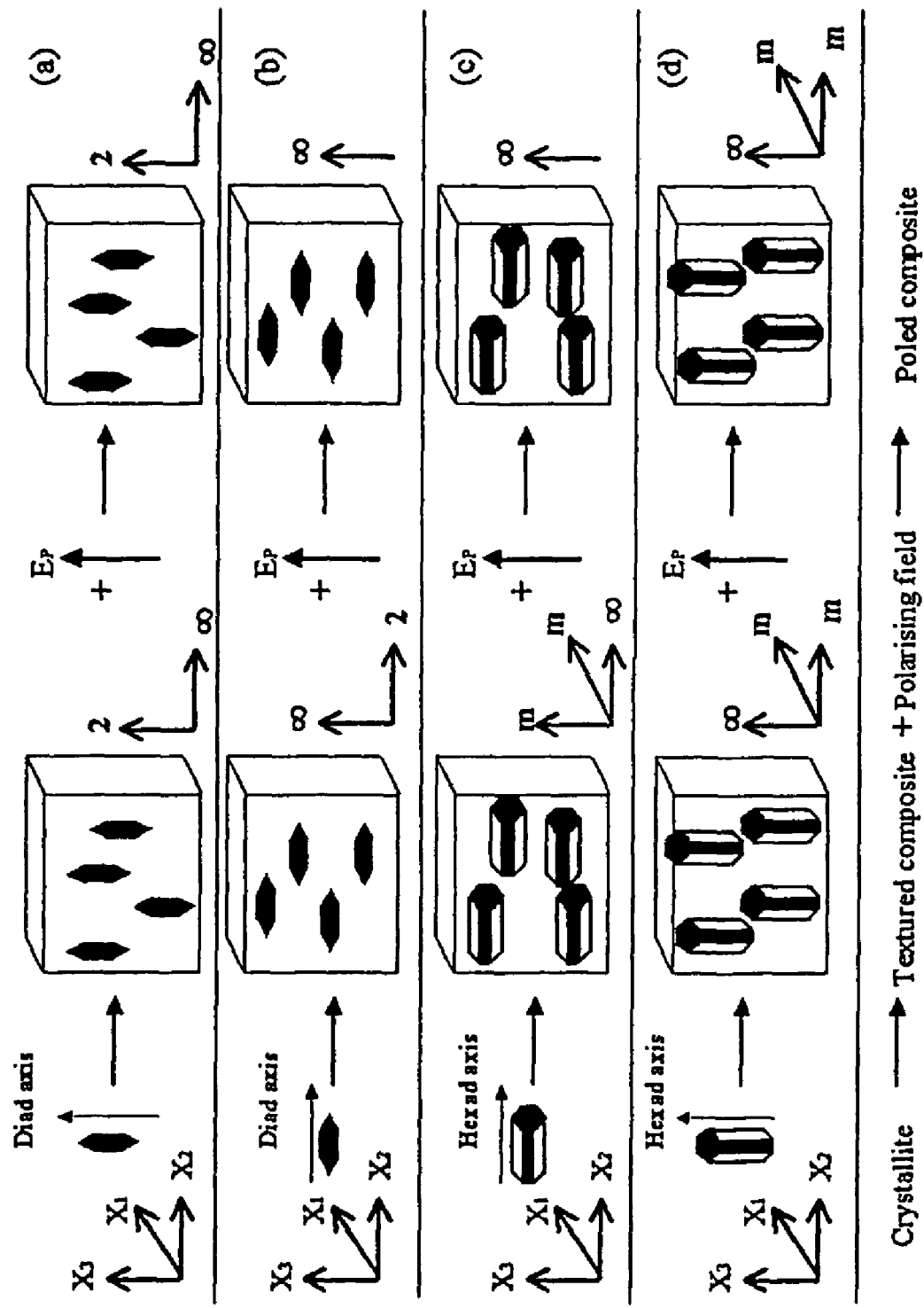
FIG. 1 is a set of diagrams showing the relationship between polarisation axes in single crystallites of HA and the macroscopic limiting group symmetries of the textured bodies in absence and presence of an electric field.

In the present invention devices comprising crystallites of HA are treated to enhance their piezoelectric properties. With reference to FIG. 1 the overall limiting group symmetry of the device changes to either ∞2 (FIGS. 1a, 1b) or ∞ mm symmetry (FIGS. 1c, 1d) depending on the extent and type of texture achieved in the device and whether the crystallites are monoclinic or hexagonal. In the former case, the polycrystalline device will exhibit piezoelectricity, while the later it will exhibit both piezoelectricity and pyroelectricity.

During poling, the device is heated to a suitable temperature (poling temperature) and an electric field is applied while the device is held at the poling temperature. The device is then cooled under field. Poling can also be achieved from contact of the HA device with an ionised gas, with or without the application of heat as for example in corona discharge poling. The time duration of poling, the poling field (magnitude and direction), and the poling temperature (if required) of textured HA devices will depend on the purity of the HA, the type of texture desired to give the relevant symmetry and on the presence of other components or constituents (if any).

Poling is an external influence and on its own will affect the overall limiting group symmetry of the HA device in accordance with Curie's principle. For example, when a HA device is subjected to an electric field vector, symmetry ∞ mm, m∞ m or mm∞, the overall limiting group symmetry of the textured devices in FIG. 1 will be reduced further to either ∞, ∞ mm or ∞2, also given in FIG. 1.

For HA single crystals segmented into domains of spontaneous polarisation, poling will orient the domains along the direction of the poling field. The new limiting group symmetry of poled HA crystal will be either ∞, ∞ mm or ∞2.

Figure 2:
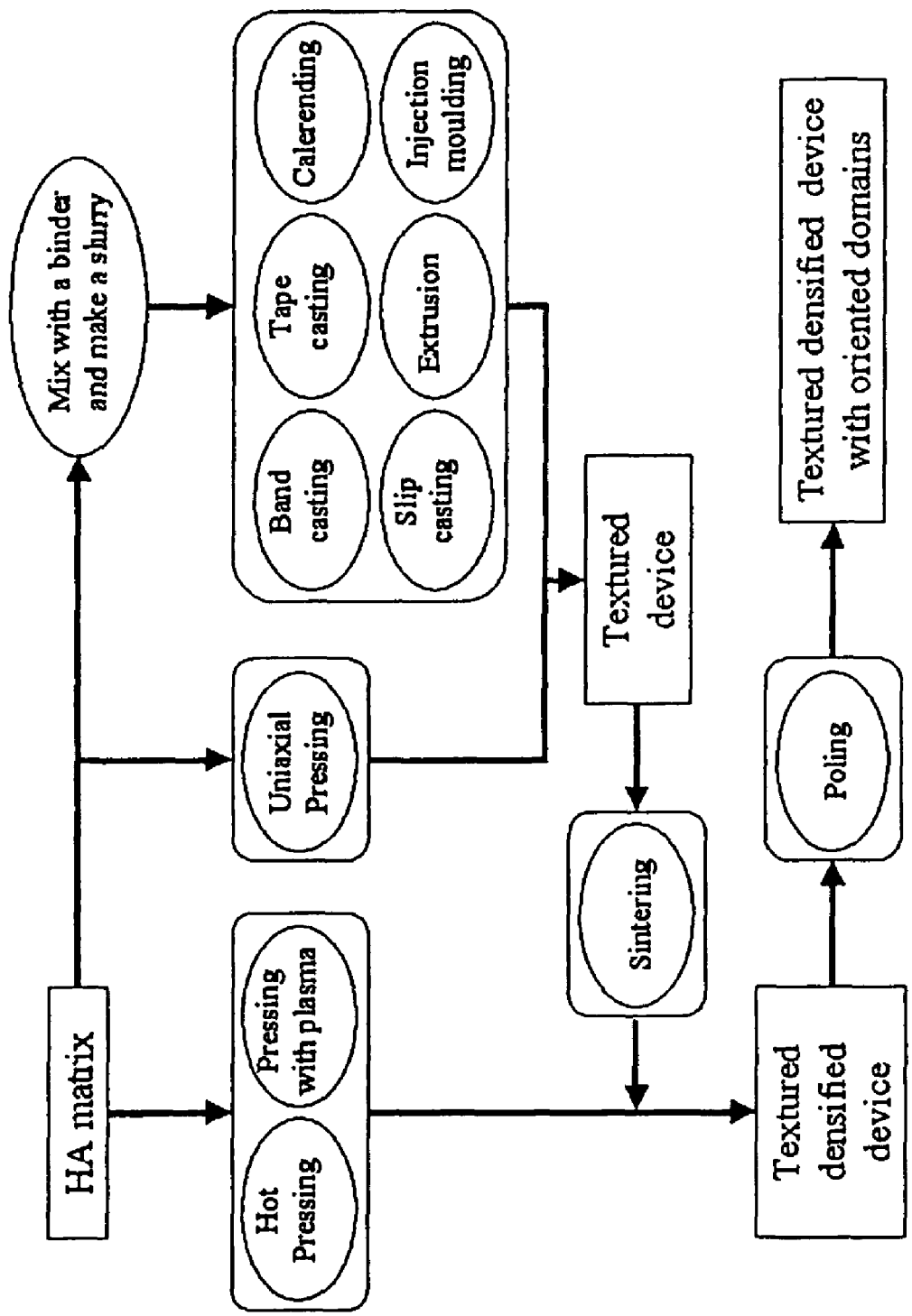
FIG. 2 is a flow diagram of various methods for texturising polycrystalline HA ceramic devices.

FIG. 2 is a flow diagram showing various process options to texturise HA to impart limiting group symmetry (henceforth limiting symmetry) ∞, ∞ mm or ∞2. In the examples described below the steps are uniaxial pressing for texturisation followed by poling. However a range of other techniques may be used for texturisation such as hot pressing, pressing in a ionised gas such as a plasma, and a variety of casting/extrusion/moulding options for a HA slurry.

Figure 3A:
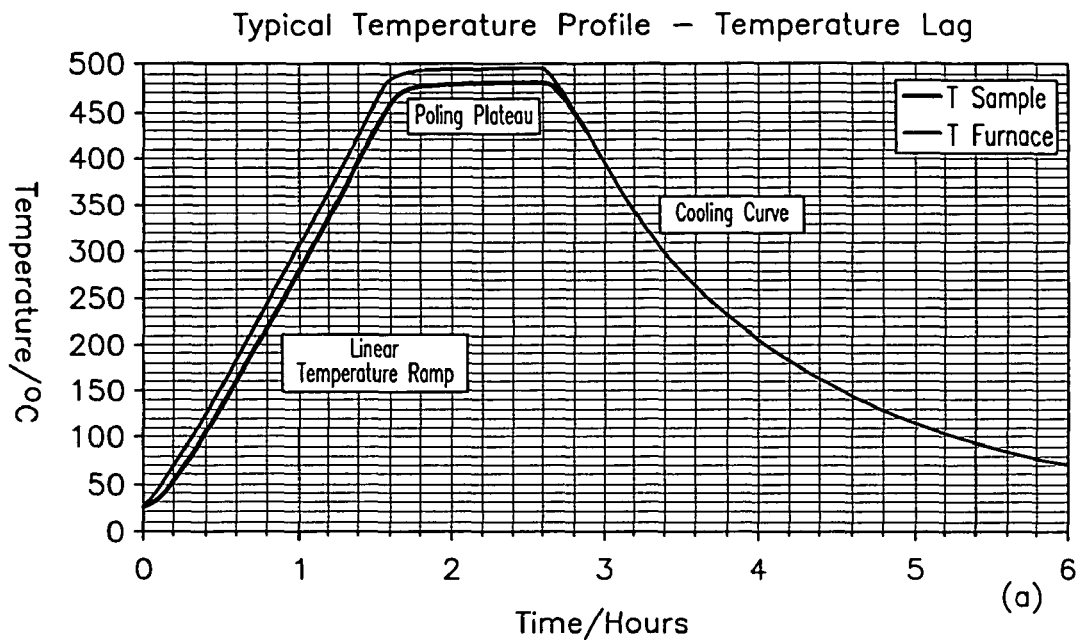
FIG. 3(a) is a lag profile showing the difference between the furnace temperature and the sample temperature in a rig used for thermoelectric treatment of samples.
Figure 3B:
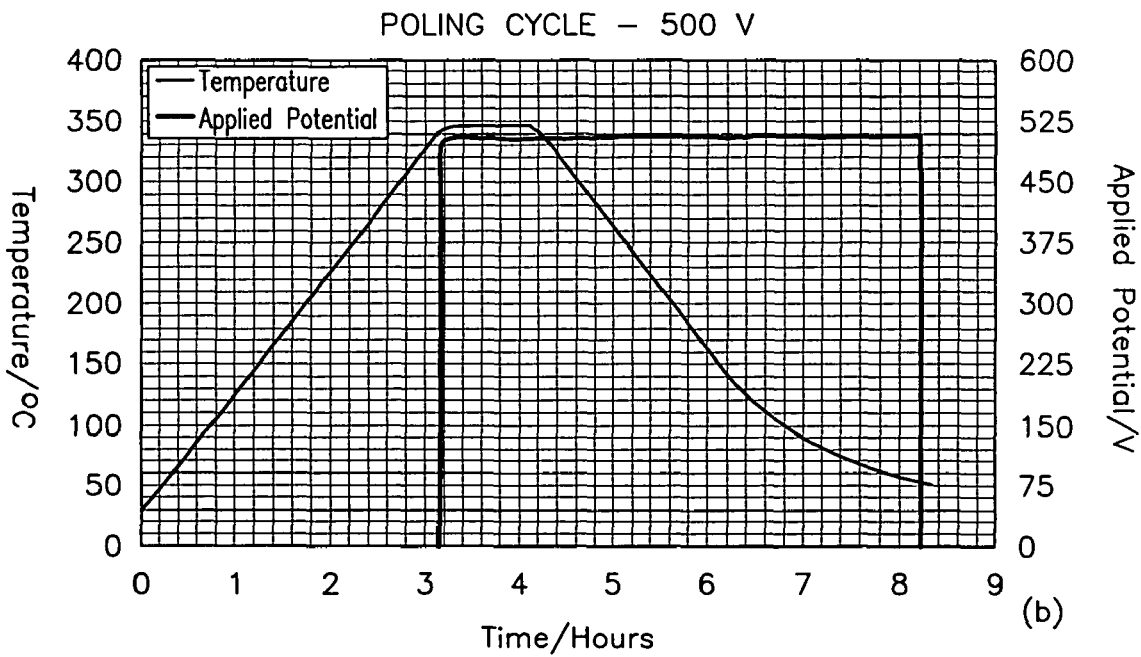
FIG. 3(b) is a time-temperature-voltage plot for a poling procedure cycle applied to a HA device.

FIG. 3(a) shows a temperature profile for poling, whereas FIG. 3(b) shows the HA temperature plateau achieved for a ramped applied potential.

Our examples show that by uniaxial pressing only, 4-20% anisotropy in various directions can be imparted in the device.

The individual piezoelectric tensors of the non-centrosymmetric single crystal hydroxyapatite phases are given in Equations 1.1 ($P2_1$, diad axis parallel to $X_2$), 1.2 ($P2_1$, diad axis parallel to $X_3$) and 1.3 ($P6_3$) respectively. Referring again to FIG. 1, in the case of polycrystalline devices, we can consider two ideal cases of orientation ascribed relative to, for example, a pressing direction or an applied field. Taking the pressing direction as $X_3$ we can consider the symmetry of the overall device when the diad or hexad axes, in the case of the monoclinic and hexagonal symmetries respectively, of the grains are parallel to $X_3$ and at the other extreme the case when the axes are in the plane perpendicular to $X_3$.

$$\begin{pmatrix} 0 & 0 & 0 & d_{14} & 0 & d_{16} \\ d_{21} & d_{22} & d_{23} & 0 & d_{25} & 0 \\ 0 & 0 & 0 & d_{34} & 0 & d_{36} \end{pmatrix} \quad 1.1$$
$$\text{monoclinic}(2\|x_2)$$

$$\begin{pmatrix} 0 & 0 & 0 & d_{14} & d_{15} & 0 \\ 0 & 0 & 0 & d_{24} & d_{25} & 0 \\ d_{31} & d_{32} & d_{33} & 0 & 0 & d_{36} \end{pmatrix} \quad 1.2$$
$$\text{monoclinic}(2\|x_3)$$

$$\begin{pmatrix} 0 & 0 & 0 & d_{14} & d_{15} & 0 \\ 0 & 0 & 0 & d_{15} & -d_{14} & 0 \\ d_{31} & d_{32} & d_{33} & 0 & 0 & 0 \end{pmatrix} \quad 1.3$$
$$\text{hexagonal}$$

The expected limiting group symmetries of the devices (determined from Curie's principle) are given in FIG. 1 for each of these scenarios. Also given in FIG. 1 are the limiting group symmetries when these textured devices are combined with an electric field applied parallel to the $X_3$ direction.

In technical applications 100% orientation of the crystallites is rarely achieved and is for practical purposes, such orientation is a theoretical possibility. Only a certain level of orientation can be achieved depending on the choice of method used to attain texture and the properties of the constituents comprising the device. For example, uniaxial pressing of pure HA powders at 100 MPa pressure, followed by subsequent densification at 1200° C., can result in 4%-20% anisotropy in the sintered body as demonstrated by elastic properties measurements in Tables 1 and 2. This scenario is shown schematically in FIG. 4(a), where the diad axes lies in the plane perpendicular to the pressing direction, $X_3$. As not all the diad axes are aligned in the same direction within this plane, not all the piezoelectric coefficients of the single crystal tensor are likely to be present. In order to determine which coefficients remain in the device, a transformation of the piezoelectric tensor is necessary. This is achieved by using an appropriate transformation matrix. An example of such a transformation matrix is given for the $P2_1$ case in FIG. 4(c). The matrix elements were determined from the relationship between a set of old axes and new axes denoted $X_1, X_2, X_3$ and $X_1', X_2', X_3'$ respectively in FIG. 4(b).

In order to determine the piezoelectric coefficients most likely to remain in the device in the case where the $P2_1$ crystals are oriented with there diad axes in the plane perpendicular to the pressing direction the single crystal tensor coefficients (d l m n) of equations 1.1 and 1.2 are transformed according to equation 1.4 and averaged over the possible values of φ (equation 1.5) to find the effective piezoelectric coefficients of the device, $d_{ia}^{eff}$.

$$d_{ijk}^{\varphi} = a_{il}a_{jm}a_{kn}d_{lmn}$$

$$d_{i\alpha} = \begin{Bmatrix} d_{ijk}, & \alpha = 1,2,3 \\ 2d_{ijk}, & \alpha = 456 \end{Bmatrix} \quad 1.4$$

$$d_{i\alpha}^{eff} = \frac{1}{2\pi}\int_0^{2\pi} d_{i\alpha}^{\varphi} d\varphi \quad 1.5$$

$$d_{i\alpha}^{\mathit{eff}} = \begin{pmatrix} 0 & 0 & 0 & d_{14}^{\mathit{eff}} & 0 & 0 \\ 0 & 0 & 0 & 0 & -d_{14}^{\mathit{eff}} & 0 \\ 0 & 0 & 0 & 0 & 0 & 0 \end{pmatrix} \quad 1.6$$

As a result of the evaluation of the integrals many of the coefficients in the single crystal tensor go to zero in the composite tensor, given in matrix form in equation 1.6. The relationship between $d_{14}^{\mathit{eff}}$ and the single crystal coefficients is given in equation 1.7.

$$d_{14}^{\mathit{eff}} = \frac{1}{2}(d_{14} - d_{25}) \quad 1.7$$

Hydroxyapatite, obtained by or derived from any route and in various forms (polycrystals, powders, granules, blocks or sintered or calcined ceramic, films, coatings, porous or non porous comprising HA or a composite in which HA is an ingredient) will become piezoelectric when the texture treatment is performed. The numerical value of the piezoelectric coefficient will depend on the extent of texture, the density and purity of HA used, porosity, connectivity and the type and amount of other constituent/s in the final product.

For devices comprised of pure hydroxyapatite, or hydroxyapatite wherein $CO_3^{-2}$ and $Na^+$, $K^+$, $Mg^{+2}$ or other cations are present as a substituent or as an impurity, such as those derived from natural sources including autografts, xenografts or allografts, the same texture treatment, when performed will enhance piezoelectricity and possibly also pyroelectricity of the derived product.

Such texture treatment can also be applied to HA devices that are derived from naturally occurring porous templates such as coral or derived by using foams or surfactants to introduce micro and macro-porosity (open, close or interconnected) in devices comprising pure or substituted HA.

This texture treatment is equally applicable to devices, where HA derived from natural or synthetic origin as mentioned above is an ingredient and the product after this treatment is piezoelectric and or pyroelectric.

The texture treatment is therefore applicable to obtain piezoelectric and in some cases also pyroelectric hydroxyapatite (hereafter PE HA) devices, in a variety of forms, with differing density, crystallinity, stoichiometry, morphology, texture, connectivity and phase.

In various embodiments the texture treatment, of HA devices can obtain PE HA composites, porous or nonporous by:

a) Uniaxial pressing HA and then firing between 800° C. and 1300° C. In one modification of this method, HA can be pre-calcined for durations over 30 minutes at temperatures lower than 900° C., ground, put in a suspension with, for example acetone, and allowed to sediment. The sediment can then be fired between 800-1300° C.

b) Restricting the flow of colloidal slurry (wherein HA is an ingredient) by for example tape casting, slip casting, calendaring, extrusion, jiggering, injection moulding, band casting or silk screening, which then can be fired between 800° C. and 1300° C. In one modification of this method, precalcined HA powder can be used and final densification can be achieved in a similar way to the uniaxial pressing method.

c) Uniaxially pressing HA at above 30 MPa pressure while firing at sintering temperature of 800° C. to 1300° C. In one modification of the process, HA powder can be uniaxially cold-pressed at above 30 MPa and then isostatically hot pressed between 800° C. and 1300° C. at pressures greater than 30 MPa.

d) Uniaxially or isostatically pressing above 30 MPa under the action of an electric field whilst sintering at 800° C.-1300° C. with or without the creation of plasma.

e) Using collagen or similar proteins of natural or synthetic origin as templates to orient HA.

Poling of HA is accomplished by the application of a pre-calculated dc-electric field, which is lower than the dielectric breakdown voltage of the sample, via electrodes while maintaining temperature of the sample at the 'poling' temperature for a pre-specified duration. The sample is then cooled to room temperature and is suitable for further application.

The direction of poling will depend on the limiting group symmetry of the HA device as illustrated in FIG. 1. The final limiting group symmetry of textured and poled HA device will depend on the direction of poling. For example, a textured HA device with ∞2 limiting symmetry when poled along the direction of the diad axis (FIG. 1(a)) will end up in a ∞2 symmetry that only allows a shear piezoelectric constant d14 and no pyroelectricity. Whereas, the same textured device, when poled in a direction perpendicular to the diad axis (FIG. 1(b)) will end up with limiting symmetry ∞, that allows two shear piezoelectric constants, $d_{14}$ and $d_{15}$ and two normal shear constants $d_{13}$ and $d_{33}$. It also contains spontaneous polarisation and thus exhibits pyroelectricity.

The poling temperature can vary according to the nature of the HA device. For devices comprising HA only, or ceramics, films or composites where other inorganic constituents, such as barium titanate, PZT or any other calcium phosphate, are present the poling can be performed by heating the device to a temperature between 40° C. and 650° C., but better results can be obtained by poling between 150° C. and 450° C. Poling can be performed for duration of 0.25 hour and 6 hour without causing the material to degrade. Good results can be obtained by poling between half an hour to 2 hours. The voltage applied for poling ranges between 0.1 kVcm$^{-1}$ and the dielectric breakdown voltage of the device. For all practical purposes, the upper limit can be taken as 90 kVcm$^{-1}$. The typical medium of poling is air. Special care is required when applying a field that is higher 30 kVcm$^{-1}$ to avoid sparking due to the breakdown of air. A suitable solution is performing the poling operation in a medium, which has higher dielectric strength than air.

In case where the device contains ingredients that denature at high temperatures, poling should be performed at lower temperatures. For example, when the HA composite comprises collagen, poling should be performed below 60° C. Poling below this temperature may take a longer time than that required in standard poling operation. In some cases, for example, where HA is blended with chitosan or PVDF, a corona discharge poling can alternatively be used to polarize the device.

Piezoelectric HA (PEHA), or materials that contain PEHA, due to its piezoelectric properties can then be used in bone graft substitutes, in various forms, states and shapes, cut or formed, polished or rough, or delivered in a slurry or paste form or through a medium. It may be implanted in hard or soft tissue or as a component in a pure or composite implant, whether in human or animal application. PEHA composites or materials containing PEHA composites can also be used for any in vivo application including trauma reduction and/or drug elution or as a carrier of bone morphogenic proteins (BMP) and/or other growth factors of any nature (synthetic or natural) in all biomedical applications including orthopaedic, dental and maxillofacial applications.

PEHA-devices possess better transducer properties in the higher frequency ultrasonic range and microwave range when compared to the performance of existing piezoelectric materials and thus can be used in medical devices.

PEHA devices produced as described above can be used as bone defect fillers, bone-cement enhancers, coating or shot-pining grits for coating or shot-blasting medical and biomedical implants or devices.

originally uniaxially pressed. A stress along the [101] direction will then generate piezoelectric charge in the (010) surface.

Further insight into the anisotropic nature of such devices comprising polycrystalline HA can be obtained from the measurement of their anisotropic elastic properties using the ultrasound method. Table 1 includes the anisotropic stiffness coefficients of HA ceramics prepared by uniaxial die pressing and subsequent densification at high temperature. Table 1 also includes the stiffness coefficients of a single crystal of hydroxyapatite and those of a completely isotropic polycrystalline composite for comparison.

TABLE 1

Stiffness matrices for hydroxyapatite, bone and tendon (units are in Gpa).

| Stiffness constant | Calculated from Fluorapatite for single crystal HA | Calculated from first principle for single crystal HA | Calculated average for completely isotropic polycrystalline HA | Ceramic HA prepared by uniaxial pressing and then sintering |
|---|---|---|---|---|
| $c_{11}$ | 137.0 | 138.0 | 159.6 | 137.2 |
| $c_{12}$ | 42.5 | 45.9 | 64.9 | 53 |
| $c_{13}$ | 54.9 | 69.1 | 57.5 | 55.1 |
| $c_{33}$ | 172 | 172.8 | 138 | 123.2 |
| $c_{44}$ | 39.6 | 51.4 | 48.7 | 42.2 |

Also, the invention shows that HA devices are possible candidates for the manufacture of opto-acoustic devices.

Figure 4:
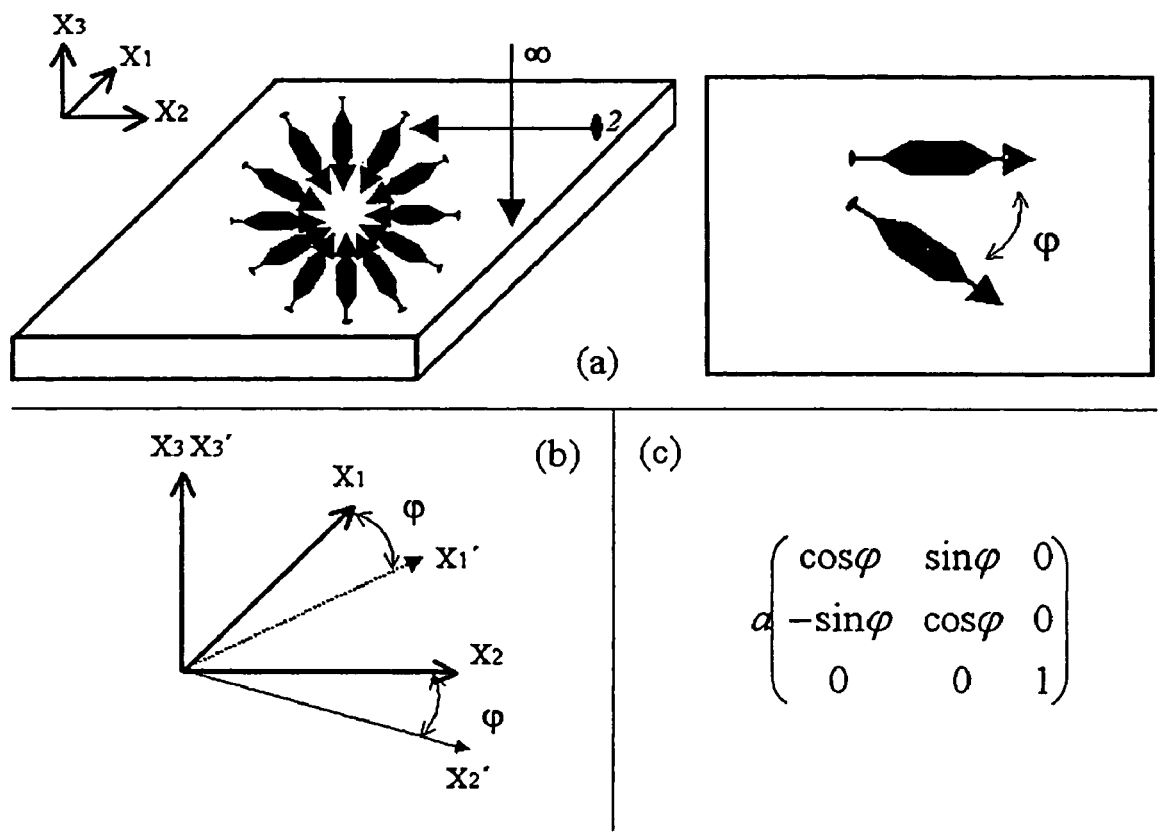

In one example, pure hydroxyapatite comprising nano-crystallites, approximately 78% of which had the $P2_1$ crystal symmetry, was uniaxially pressed in an 8 mm diameter circular die at a pressure of 75 MPa. The pressing direction is taken as the [001] direction in the ceramic, which is denoted as the '3' direction in FIGS. 5 and 6. The resulting disks were sintered at 1200° C. for one hour to give a sintered ceramic approximately 6 mm in diameter. The ceramic density was 98% of the theoretical density. The limiting symmetry of the ceramic was ∞2 (FIG. 4). From a 2D-texture analysis using a scanning electron microscope, the average angular orientation of HA grain projections on the [001] surface and their average shape anisotropy (ratio of two perpendicular grain dimensions) were found to be 83° (90° means no preferred in-plane grain axis orientation) and 1.45 (where 1 means no shape anisotropy, i.e. spherical grains). This reveals a level of anisotropy in the HA device, induced by uniaxial pressing.

In order to measure the effective $d_{14}^{eff}$ coefficient of the ceramic, which is equal in magnitude but opposite in sign to the $d_{25}^{eff}$ coefficient, samples were cut from the ceramics, as illustrated in FIG. 5, hereafter referred to as [101] samples. Two types of measurements were carried out. In the first case a voltage across the (010) facets in response to a quasistatic force (219 mN in amplitude at a frequency of 110 Hz) applied in the [101] direction i.e. the (010) facets were electroded. In the second case a current was measured with a quasistatic force of amplitude 216 mN at a frequency of 110 Hz. The measured value of the piezoelectric strain coefficient, $d_{14}$, was 0.01 pC N$^{-1}$ form a voltage reading, while a value of 0.019 pC N$^{-1}$ was measured using a current reading. Of considerable importance is that the polarity of the measured voltages and currents changed in accordance with the reversal of the sense of the applied quasistatic force.

Referring again to FIG. 5, for the measurement of the effective piezoelectric constant, $d_{14}^{eff}$, this HA requires to be faceted along the [101] direction as required by the ∞2 symmetry. This can be achieved from a sintered sample by cutting 45° facets to the '3' direction along which the sample was The percentage deviation of the experimentally measured values from those of the single crystals (calculated from fluorapatite data and from first principle) and the polycrystalline average are listed in Table 2. The anisotropic nature of the pressed device is manifest in the deviation (~12% on an average) of the coefficients from those of the polycrystalline aggregate with random orientation of the individual grains.

TABLE 2

Deviation of the stiffness constants of uniaxially pressed HA ceramic from those of calculated and single crystal values

| | % Deviation of stiffness constants from calculated stiffness | | |
|---|---|---|---|
| Stiffness constant | From Fluorapatite | From First Principle | Calculated average for polycrystals |
| $c_{11}$ | −0.1 | 0.6 | 14.0 |
| $c_{12}$ | −24.7 | −15.5 | 18.3 |
| $c_{13}$ | −0.4 | 20.3 | 4.2 |
| $c_{33}$ | 28.4 | 28.7 | 10.7 |
| $c_{44}$ | −6.6 | 17.9 | 13.3 |

A detailed consideration of the effective symmetry of the HA ceramic reveals that while both the quasi-longitudinal and quasi-transverse modes of ultrasound wave propagation in [101] samples of HA are independent of piezoelectric contributions, the transverse mode ($\Gamma_{22}$) represents a piezoelectrically clamped condition. Knowledge of the clamped permittivity, relevant elastic stiffness constants and the velocity of this ultrasound mode thus provide a means to measure the piezoelectric $e_{14}$ constant of a completely textured HA device belonging to ∞2 limiting symmetry according to the following Equation 1.8

$$\Gamma_{22} = \frac{1}{2}\left(c_{44}^E + c_{66}^E + \frac{e_{14}^2}{\varepsilon_{11}^S + \varepsilon_{33}^S}\right) \qquad 1.8$$

Here, $\Gamma_{ij}$ are the Cristoffel's tensor elements, $c_{ij}$ are shear stiffness coefficients with $c_{66}=\frac{1}{2}(c_{11}-c_{12})$, and $\in^s_{11}$ and $\in^s_{33}$ are the clamped permittivities in the [100] and [001] directions respectively. Based on ultrasound propagation in the ceramic hydroxyapatite, the technique gives a value of 0.606 C m$^{-2}$ for the piezoelectric stress coefficient. The value of the corresponding piezoelectric strain constant $d_{14}$ is about 14 pC N$^{-1}$, the upper limit calculated from ultrasound measurements.

Pyroelectricity Measurements

In another example, approximately 1.5 g of pure hydroxyapatite was uniaxially pressed under a load of 100 MPa in a cylindrical die to make a HA cylinder approximately 8 mm in diameter and 1 cm in height. The cylinder was then sintered at 1200° C. for one hour to obtain a ceramic 6 mm in diameter and 8 mm in height. A thin disc of approximately 1.5 mm thickness was then cut from the cylinder. FIG. 6 shows the orientation of the disk with respect to the pressing direction [001] along the axis '3'. The limiting symmetry of the unpoled sample was ∞2. The sample was then electroded on the (001) surfaces, so that the sample can be poled along the ∞-axis of symmetry (FIG. 4) of the device and so the poling field becomes perpendicular to the diad axis. According to FIG. 1(*b*) such a configuration of poling should result in a poled HA device with limiting symmetry ∞ that allows pyroelectricity. The polarizing field will orient the dipoles in the textured HA device along the poling direction. The poled HA device will thus have a spontaneous polarisation along the poling direction. This is illustrated in FIG. 7. Although the following example describes a disk sample, similar results will be obtained for a thin plate faceted from the disk sample as shown in FIG. 6.

The HA disk was thermally preconditioned by heating it to 200° C. at a heating rate of 5° C. min$^{-1}$ and then cooling back to room temperature. The sample was then subjected to a poling treatment by heating it to 350° C. at which temperature an electric field of 2 kVcm$^{-1}$ was applied for the duration of one hour. The sample was then cooled down to 180° C., the temperature at which the electric field was switched off. The sample was then cooled to room temperature.

To demonstrate pyroelectricity in HA devices, it is important to separate two contributing processes: one is irreversible and the other is reversible. A thermally stimulated depolarization current (TSDC) measurement, method in conjunction with thermal cycling has been used to separate these two effects. In the TSDC method, discharged current from a sample is measured while the sample is being heated. Pyroelectricity in HA is reversible as it originates from the anisotropy of individual crystals and in the case of a sintered ceramic the anisotropic texture arising from the orientation of the crystallites. On the other hand, the presence of induced dipoles in HA as a result of poling will manifest a discharge current on heating through a first temperature cycle post the poling step as a result of the relaxation of said dipoles. However, if the discharged current is measured in a subsequent heating cycle i.e. the sample is cooled down and heated again without further poling, this initial effect of dipole relaxation will be significantly if not completely diminished. In contrast if the sample is pyroelectric this property will not be removed by the initial temperature cycle and a pyroelectric current will remain.

In the present example, a poled HA sample was subjected to two temperature cycles. The first cycle was discontinued at 350° C. as soon as the thermally stimulated dipole reorientation peak has been observed and the sample was cooled to RT. In the second cycle, heating was continued up to 500° C. at which point the sample was held for approximately 35 minutes. The sample was then cooled down to room temperature.

The discharged current spectra are shown in FIG. 8. It can be seen that the first relaxation peak has been significantly decreased in the second cycle thus indicating the exhaustion of injected charge as a result of the poling process. Of particular importance is the change in polarity of the discharge current in the second cycle, which eventually reaches a maximum value of −0.65 nA. That this current is coming from the pyroelectric nature of the HA devices can also be evidenced from a switching of the polarity of current at the onset of cooling, during which the discharge current reaches a positive maximum of 0.285 nA. This switching is expected, as the gradient of temperature (dT/dt) during cooling is opposite in sign to that during heating. In this experiment, the peak relaxation current measured during the first cycle was only 97 pA. The switch in the polarity of the measured current in response to a corresponding change in the sign of the gradient can only be explained by the pyroelectric effect.

Pyroelectricity is exhibited by a limited number of piezoelectric materials. Consequently that such HA devices are pyroelectric further establishes the fact that they are piezoelectric.

The invention is not limited to the embodiments described but may be varied in construction and detail.

The invention claimed is:

1. A method of producing a piezoelectric device, the method comprising the steps of
   a. providing a material comprising a polycrystalline HA component,
   b. texturing the material by uniaxially pressing the material to impart one of the limiting symmetries ∞ mm, ∞, or ∞2 to the HA component,
   c. faceting the textured material at 0°, 45°, or 90° to a texturing direction depending on the limiting symmetry imparted by texturing, and
   d. poling the textured and faceted material by applying an electric field between 0.1 kVcm$^{-1}$ and 90 kVcm$^{-1}$, the direction of poling depending on the limiting symmetry imparted during texturing.

2. The method as claimed in claim 1, wherein the uniaxial pressing comprises application of a uniaxial pressure between 30 MPa and 250 MPa, and preferably between 50 MPa and 150 MPa.

3. The method as claimed in claim 1, wherein the uniaxially pressed material is fired between 800° C. and 1700° C., preferably between 1000° C. and 1300° C.

4. The method as claimed in claim 3, wherein the uniaxially pressed material is fired in a steam environment.

5. A method as claimed in claim 3, wherein an electric field is applied during firing.

6. The method as claimed in claim 3, wherein an electric field is applied in an environment of ionised gas during firing.

7. The method as claimed in claim 6, wherein the electric field is lower than the dielectric breakdown voltage of the material, between 0.1 kVcm$^{-1}$ and 90 kVcm$^{-1}$.

8. The method as claimed in claim 1, wherein the poling step comprises heating the material to a poling temperature, holding the material at the poling temperature for a poling period, and cooling the device back to a starting temperature.

9. The method as claimed in claim 1, wherein the poling step comprises heating the material to a poling temperature, holding the material at the poling temperature for a poling period, and cooling the device back to a starting temperature; and wherein the poling temperature is between 40° C. and 650° C., and preferably between 150° C. and 450° C.

10. The method as claimed in claim 1, wherein the poling step comprises heating the material to a poling temperature, holding the material at the poling temperature for a poling period, and cooling the device back to a starting temperature; and wherein the poling period is between 0.25hr and 6hr and preferably between 0.5hr and 2.0hr.

11. The method as claimed in claim 1, wherein the HA component is anisotropic.

12. The method as claimed in claim 11, wherein the anisotropy is over 5%.

* * * * *